United States Patent [19]

Lahr et al.

[11] Patent Number: 5,071,642
[45] Date of Patent: Dec. 10, 1991

[54] DIHYDROPYRIDINE CONTAINING COMPOSITIONS

[75] Inventors: Wolfgang Lahr, Laupheim; Hans Köhne, Obersulmetingen; Frank Musculus, Achstetten; Hein-Uwe Schmersahl, Limesharn, all of Fed. Rep. of Germany

[73] Assignee: Dr. Rentschler Arzneimittel GmbH & Co., Laupheim, Fed. Rep. of Germany

[21] Appl. No.: 111,623

[22] Filed: Oct. 21, 1987

[30] Foreign Application Priority Data

Oct. 23, 1986 [DE] Fed. Rep. of Germany ....... 3636123

[51] Int. Cl.$^5$ .......................................... A61K 31/455
[52] U.S. Cl. ..................................... 424/474; 514/19; 514/356; 514/302

[58] Field of Search ......................... 514/19, 302, 356; 424/78

[56] References Cited

U.S. PATENT DOCUMENTS 4,562,069 12/1985 Hegasy et al. ...................... 514/356
4,703,038 10/1987 Garthoff et al. ...................... 514/19

FOREIGN PATENT DOCUMENTS 0248548 12/1987 European Pat. Off. .

Primary Examiner—Prince E. Willis
Assistant Examiner—John F. McNally
Attorney, Agent, or Firm—Cohen, Pontani & Lieberman

[57] ABSTRACT

Solid drug formulations for oral administration containing one or more dihydropyridines in doses of between 10 and 240 mg and suitable to be administered as a single dose per day for the treatment of circulatory disorders and high blood pressure.

11 Claims, No Drawings

DIHYDROPYRIDINE CONTAINING COMPOSITIONS

FIELD OF THE INVENTION

The present invention relates to new solid drug formulations for oral administration, methods for the preparation thereof, and their use for the treatment of circulatory disorders. The formulations contain one or more dihydropyridines in doses of between 10 and 240 mg and are suitable for administration as a single dose per day. The production of dihydropyridines such as, for example, nifedipine as well as nifedipine-related substances is known from British Patent 11 73 862.

BACKGROUND ART

Dihydropyridines are used for the treatment of circulatory disorders and high blood pressure and are highly effective substances which, because of their side effects, must be administered to the patient specifically adapted in accordance with the clinical picture and individual need of the patient for the drug. From British Patent 11 73 862 it is known, for instance, that nifedipine, i.e. 4-(2-nitrophenyl)-2, 6-dimethyl-3, 5-dicarbomethoxy-1, 4-dihydropyridine, is to be administered orally in a dose of 2.5 mg per patient. For the treatment of angina pectoris, three doses per day, referred to patients of a weight of 70 kg, are to be given. This dose can be increased or reduced depending on the response of the patient. If larger doses are administered, they should be given in the form of several individual doses. Known adverse effects are nausea, dizziness, fatigue, skin reactions, tingling of the arms and legs, reduction of blood pressure below normal values, heart palpitation and increase in pulse rate. Nifedipine and its derivatives have biological half-lives which may differ under pathophysiological circumstances. Thus elimination half-lives of from 2 to 3 hours up to 4 to 11 hours are indicated for nifedipine. For other dihydropyridines such as nitrendipine, 6 to 15 hours are indicated and for nimodipine 1.5 to 2 hours and up to 22 hours in the case of chronic renal insufficiency with a creatinine clearance of less than 30 ml per minute.

These biopharmaceutical data indicate to tne skilled person that the producing of a steady state in the organism between the amount of active substance absorbed and the amount eliminated is problematical, for instance, in the case of nifedipine and its derivatives. In particular, an individual determination of the dose is needed for each patient in order to obtain therapeutically effective blood levels. Thereby it is necessary to dose in such a way that a reasonable ratio of effect to side effect is maintained.

This is imperfectly achieved, for instance, for nifedipine by the known initially liberating drug forms (chewable capsules, Federal Republic of Germany Patent 22 09 529). These initially acting forms for administration permit the active substance in the blood to increase rapidly to a high level up to peak concentrations which, as a rule, are not required for the treatment, then rapidly dropping again to sub-therapeutic concentrations (Dtsche Apoth. Ztg. 125 (1985), pages 1174–1176, FIG. 1). As compared with the minimum therapeutically active plasma concentration of 10-15 nanograms/ml (Selecta 10 (1983), page 860), that article mentions concentrations of up to 185 nanograms/ml. It follows from this that another dose must be administered again at the latest within three to four hours. Obviously with initially liberating forms of this kind, assured treatment can be obtained only with a large number of individual doses.

Drugs which must be administered several times a day for proper therapeutic treatment are frequently converted into formulations having a retarded, i.e. delayed, characteristic of liberation. Retardation is meaningful if the elimination halflife of the active substance is sufficiently short and/or the regularity of ingestion (patient compliance) is to be improved by this measure. The purpose of retardation is to form, after repeated administration a uniform, therapeutically active blood level with the lightest possible variation between $C_{max}$ and $C_{min}$ (i.e. between maximum and minimum blood level concentrations).

Thus different retard forms and methods for the manufacture thereof are known also for nifedipine and its derivatives.

British Patent 20 53 681 describes retard formulations for the dihydropyridines nicardipine and nifedipine in which the substance in question is present in amorphous form together with polyethylene oxide and other adjuvants.

In Federal Republic of Germany OS 30 24 858, the German counterpart of British Patent 20 53 681, additional results of a bioavailability as compared with the control, nevertheless clearly show that the blood levels drop after at most 6 hours.

British Patent 21 59 407 describes a solid nifedipine formulation using casein and inorganic adjuvants. It is evident from the bioavailability testing that uniform blood levels are obtained for a period of 4-6 hours, followed by a rapid decline (FIG. 7).

European Patent A-00 47 899 teaches the production of nifedipine-containing solid drug formulations in which the active substance is present with a well-defined specific surface. Use is made of the self-retardation of practically water-insoluble nifedipine crystals (slow dissolving of the crystals).

The indicated plasma concentrations show for Example 1 of EP-A-00 47 899, a rapid surge after the first hour and a plateau-like course for the second to eighth hours, followed by a rapid decline to a lower level. The curve for Example 2 shows a plateau from the first to the sixth hours, followed by a decline.

In addition, the state of the art is formed by the preparations available on the market and their dosage recommendations. All known nifedipine retard preparations are taken, according to the information given by the manufacturer, one tablet two times a day up to four times a day with an interval of 4 to 12 hours between tablets. The nifedipine derivative nimodipine is administered orally as Nimotop ® in six hour intervals four times a day with 2 tablets of 30 mg each (Red List 1986, Consecutive No. 26084).

For commercial nifedipine-containing retard forms it is shown, on the basis of a bioavailability study, that despite retardation the active substance rapidly increases to peak concentrations (which are far above the therapeutically required concentrations) and, at the latest within 10 hours, the concentration drops below the minimum therapeutic level of activity (Arzneim.-Forsch./Drug Res. 35 (II), No. 12, 1983, pages 1840–1842).

It follows from these data and measurement results that, while it is possible to retard nifedipine and its related substance in order to obtain blood level concentrations which are retained for a long time, nevertheless these attempts have remained imperfect, as shown in practical use.

DISCLOSURE OF THE INVENTION

It was therefore surprising to find that it is possible to retard dihydropyridines for oral administration in such a manner that after the use of such preparations in humans uniform, i.e. plateau-like, blood level curves can be measured for more than 12 hours, i.e. for up to 24 hours.

It was furthermore surprising that such drug formulations containing amounts of active substance which are far above the previously customary doses, namely amounts of 10 to 240 mg and preferably 30 to 120 mg and especially 40 to 80 mg per individual dose, can be administered without the occurrence after ingestion of the adverse effects described above which are specific to these substances, particularly at peak blood level concentrations.

It was furthermore surprising that the blood level of the active substance from the drug formulations of the invention increases slowly within the organism, depending on the quantitative and qualitative composition of the adjuvants, so that pronounced blood level maxima, i.e. blood level peaks, are avoided but nevertheless therapeutically active blood levels are obtained.

It was also unexpected that the above-described effects of the drug formulations of the invention would occur since in vitro the active substance shows the liberation behavior which is customary for conventional retard forms.

The finding was also new and surprising to the person skilled in the art that these advantageous effects occur if the dihydropyridines used in accordance with the invention are present in the form of administration in dissolved, molecularly dispersed state, i.e. as solid solution. It would have been expected that the substances, which are per se practically insoluble, would be particularly rapidly absorbed in noncrystalline state, as appears from EP-A-01 67 909, and would then be eliminated correspondingly rapidly. A typical example of a rapidly rising blood level concentration is described in Federal Republic of Germany OS 33 26 167. The glibenclamid used therein is practically water-insoluble, similar to the dihydropyridines used in the present invention. By converting this substance into the noncrystalline state a rapid increase of the active substance within the blood plasma as well as the desired peak concentrations are obtained.

DESCRIPTION OF THE PREFERRED EMBODIMENT

The drug formulations of the present invention contain, in essence, one or more dihydropyridine to be retarded and a fatty alcohol or fatty-alcohol mixture as a shaping matrix. As solvents for the dihydropyridine there are preferably used polyethylene glycols of molecular weights of 200 to about 35,000. In order to improve the solubility of the dihydripyridine in the solvent, polyethylene glycol, one or more solubilizing adjuvants can be added, particularly when high-molecular polyethylene glycols are used or when the dihydropyridine tends to recrystallize in the drug form.

The dihydropyridines are present in each form of administration in accordance with the present invention in quantities of 10 to 240 mg, preferably 30 to 120 mg, and especially 40 to 80 mg. As dihydropyridines in addition to nifedipine-like substance such as, for example, nimodipine, nitrendipine, nicardipine, nisoldipine and felodipine are also used.

The polyethylene glycols having molecular weights of 200 to about 35,000 are used either as molecular fractions which can be considered uniform or in the form of mixtures of different molecular fractions, the preferred ratio by weight or dihydropyridine to polyethylene glycol being 1:2 to 50 and particularly 1:4 to 1:40. As matrix-forming fatty alcohol, saturated fatty alcohols which may be solid or liquid at room temperature are preferably used, particularly those with chain lengths of 6 to 30 carbon atoms. Weight ratios of tne dihydropyridine to fatty alcohol of 1:0.1 to 1:10 and particularly 1:1 to 1:3 are preferred.

In order to obtain solid drug forms, polyethylene glycols which are solid at room temperature are used when liquid fatty alcohols are employed, and vice versa. It is, however, possible to mix solid fatty alcohols with solid polyethylene glycols. The mixtures are, if necessary, prepared above the melting point. As solubilizing adjuvants which enter into consideration for improving the solubility of dihydropyridine in the polyethylene glycols are suitable all those which do not have a stability-reducing effect on the forms in accordance with the present invention and are to be considered pharmacologically compatible. Such substances are, as is known, polyvinylpyrrolidones, polyoxyethylene fatty alcohol ethers, polyoxyethylene sorbitan fatty acid esters, polyoxyethylene stearic acid esters, Pluronics ®, fatty alcohol sulfates and other surface-active agents. If such solubilizing substances are used then, as a rule, weight ratios of dihydropyridine to solubilizer of 1:0.1 to 1:3 are sufficient.

In addition, the drug preparations of the present invention can contain further adjuvants such as, for instance, coloring substances, glidants and lubricating agents, disintegrants, fillers, softeners and the like.

The formulations of the present invention are produced by known methods, in the manner that the dihydropyricine is dissolved in the selected polyethylene glycol, if necessary with heat. The fatty alcohol is added to this mixture so that, as a rule, a clear melt is present. A solubilizing component and, optionally, other adjuvants may be added. These mixtures are highly viscous to solid at room temperature and can thus be worked into forms of administration. Preferred forms of administration of the drug formulations of the present invention are tablets, capsules, pills, coated tablets, sachets, multilayer tablets and granulates, the production of which is effected by known methods. Since dihydropyridines are sensitive to light, all work is carried out protected from light.

The drug formulations of the invention can possibly be combined with other therapeutically meaningful active substances such as, for example, alpha blockers, beta blockers and diuretics, for example in multi-layer tablets, capsules, etc. Insofar as it is therapeutically desired, several of the dihydropyridines which have been mentioned by way of example can also be combined with each other.

The following examples are intended to explain the composition and method of preparing the formulations of the invention on the basis of nifedipine as illustrative dihydropyridine.

EXAMPLE 1

| | |
|---|---|
| Nifedipine | 10.0 g |
| Polyethylene glycol (average molecular weight 200) | 80.0 g |
| Polyethylene glycol (average molecular weight 6,000) | 30.0 g |
| Stearyl alcohol | 30.0 g |
| Polyvinylpyrrolidone | 5.0 g |

The two polyethylene glycols are mixed together with heating and the nifedipine is dissolved therein with stirring. The stearyl alcohol is added to the melt and also melted. After addition of the polyvinylpyrrolidone the still-liquid mass is poured into hard gelatin capsules, size 3, in an amount of 310 mg, corresponding to 20 mg of nifedipine.

EXAMPLE 2

| | |
|---|---|
| Nifedipine | 10 g |
| Polyethylene glycol (average molecular weight 200) | 90 g |
| Polyethylene glycol (average molecular weight 20,000) | 25 g |
| Stearyl alcohol | 30 g |

The preparation is effected in a manner similar to Example 1. The melt is filled into hard gelatin capsules, size 1, in an amount of 465 mg, corresponding to 30 mg of nifedipine.

EXAMPLE 3

| | |
|---|---|
| Nifedipine | 10 g |
| Polyethylene glycol (average molecular weight 200) | 90 g |
| Octyl alcohol | 15 g |

The nifedipine is stirred into the molten polyethylene glycol and dissolved. The fatty alcohol is then added. The melt is poured into hard gelatin capsules, size 0, in an amount of 620 mg, corresponding to 40 mg of nifedipine.

EXAMPLE 4

| | |
|---|---|
| Nifedipine | 40 g |
| Polyethylene glycol (average molecular weight 6,000) | 440 g |
| Stearyl alcohol | 120 g |
| Polyvinylpyrrolidone | 20 g |

The melt is prepared in the manner indicated in Example 1. The melt is then poured out and after hardening is comminuted by means of a screening machine to an upper particle size of 1.0 mm.

The ground powder is mixed with 1% by weight each of magnesium stearate and colloidal silica. The mixture is compacted to form oblong tablets containing 60 mg nifedipine.

EXAMPLE 5

| | |
|---|---|
| Nifedipine | 60.0 g |
| Polyethylene glycol (average molecular weight 2,000) | 450.3 g |
| Stearyl alcohol | 112.6 g |
| Polyoxyethylene stearic acid ester (Myrj ® 59) | 75.1 g |

The preparation of the melt and of the tablets having a content of 60 mg of nifedipine per tablet is effected in a manner similar to Example 4.

EXAMPLE 6

| | |
|---|---|
| Nifedipine | 40.0 g |
| Polyethylene glycol (average molecular weight 2,000) | 262.5 g |
| Stearyl alcohol | 75.0 g |
| Polyoxyethylene sorbitan fatty acid ester (polysorbate 80) | 87.5 g |

The melt is prepared in a manner similar to Example 5. The melt is filled into hard gelatin capsules, size 1, with a nifedipine content of 40 mg.

In Vitro Liberation Rates

The liberation behavior of the active substance from the drug forms was tested in accordance with the US Pharmacopoeia. The pH of the liberation medium was maintained constant at 1.5 (values given in % of the amount of active substance present in each case).

As comparison there was used an ordinary commercial retard tablet (Adalat ® retard, 20 mg).

TABLE 1

| | Ex. 1 % | Ex. 2 % | Ex. 3 % | Ex. 4 % | Ex. 5 % | Ex. 6 % | Control % |
|---|---|---|---|---|---|---|---|
| 1 h | 13 | 15 | 19 | 21.5 | 12 | 25 | 23 |
| 2 h | 22 | 23 | 25 | 41 | 17 | 31 | 45 |
| 3 h | 34.5 | 28 | 36 | 55 | 24 | 40 | 57 |
| 4 h | 48 | 34 | 47 | 65 | 28 | 46 | 66 |
| 5 h | 60 | 44 | 56 | 72 | 34 | 51 | 71 |
| 6 h | 69 | 53 | 68 | 77 | 37 | 55 | 74 |
| 7 h | 81 | 62 | 79 | 81 | 40 | 59 | 76 |

Examples 1 to 6 show no substantial differences from the control in liberation behavior which demonstrates that blood levels are maintained for a longer period than heretofore produced in vivo in the prior art.

The formulations of the present invention were tested as to their bioavailability on test subjects.

EXAMPLE 7

The drug form in accordance with Example 1 was tested on each of four healthy volunteers of an age of between 18 and 40 years. They received 2 capsules of 20 mg each as single dose corresponding to 40 mg nifedipine, or 3 capsules of 20 mg each as single dose corresponding to 60 mg nifedipine. At given time intervals, blood was taken from the antecubital vein and the plasma examined for nifedipine by selective HPLC determination.

Results

| Time (hours) | 0.5 | 1 | 2 | 3 | 4 | 6 | 9 | 12 | 24 | 36 |
|---|---|---|---|---|---|---|---|---|---|---|
| 40 mg average of N = 4 (ng/ml) | 4.5 | 6.9 | 8.3 | 6.3 | 6.5 | 4.7 | 5.8 | 6.6 | 4.6 | 1.8 |
| 60 mg average of N = 4 (ng/ml) | 8.9 | 10.4 | 12.6 | 9.9 | 8.6 | 11.1 | 8.7 | 10.1 | 7.7 | 2.5 |

The plasma concentrations measured show that upon a single administration of 40 ti 60 mg nifedipine, contrary to expectations based on the prior art, no peak concentration are developed but rather uniform values (plateau) for 24 hours.

EXAMPLE 8

The drug form of Example 2 in accordance with the present invention was tested on each of four healthy volunteers of an age of 18 to 40 years. The volunteers received a single dose of one capsule of 40 mg nifedipine.

| Time (hours) | 0.5 | 1 | 2 | 3 | 4 | 6 | 9 | 12 | 24 | 36 |
|---|---|---|---|---|---|---|---|---|---|---|
| 40 mg average of N = 4 (ng/ml) | 0 | 3.3 | 2.7 | 5.5 | 4.7 | 5.4 | 14.5 | 17.7 | 10.5 | 5.4 |

EXAMPLE 9

From the data of the individual test subjects of Example 8, the steady state was calculated by means of ordinary computer programs (TOPFIT) on a WANG PC.

It was found that a steady state is obtained after only three applications of one capsule a day each.

The corresponding plasma concentrations $C_{max}$ and $C_{min}$ move within 24 hours between 16 and 24 ng/ml, i.e. within the therapeutic range.

The therapeutic effectiveness of the drug forms of the invention is demonstrated below.

EXAMPLE 10

A male hypertensive patient, 48 years of age, weight 87 kg, with morning high blood pressure before the start of the treatment of about 190 mmHg systolic and about 115 mmHg diastolic was treated with a nifedipine-containing preparation in accordance with the prior art (Adalat ® 20 retard) in accordance with the dose recommendation, with 2 × 10 mg per day at intervals of 12 hours.

An adequate reduction of the blood pressure was not obtained so that the dose was increased to 3 × 20 mg per day. After a ten-day period of treatment, the drug was discontinued for three days in order to restore the initial hypertensive condition. The treatment was then resumed with 1 × 60 mg of the drug form according to Example 4. The dose was given in each case in the morning.

The following blood pressures were measured:

|  | 1 × 60 mg nifedipine according to Example 4 | 3 × 20 mg nifedipine Adelat ® 20 mg retard |
|---|---|---|
| Blood pressure systolic | 145-155 mmHg | 150-165 mmHg |
| Blood pressure diastolic | 90-95 mmHg | 90-95 mmHg |
| Pulse rate | Increase from 85 to 90-93 during the course of the day | Increase from 85 to 100-105 in each case 3 hours after ingestion |
| Subjective adverse effects | None | Congestion in the head |

The measured therapeutic effect of the form according to the invention as compared with standard treatment with a standard drug confirms the advantageous nature of the new drug formulation.

Other examples will serve to further explain the subject matter of the invention:

EXAMPLE 11

| Nicardipine hydrochloride | 18.0 g |
|---|---|
| Propylene glycol | 36.0 g |
| Polyethylene glycol (average molecular weight 6,000) | 132.0 g |
| Stearyl alcohol | 36.0 g |
| Polyvinylpyrrolidone | 6.0 g |

Propylene glycol is heated to about 75° C. and nicardipine is dissolved therein. At the same temperature, polyethylene glycol and stearyl alcohol are added one after the other to the solution and melted. Polyvinylpyrrolidone is added to the clear mixture. The melt is filled into hard gelatine capsules of size 0 to a filling weight of 747 mg, corresponding to 59 mg of nicardipine per capsule.

EXAMPLE 12

| Nicardipine hydrochloride | 18.0 g |
|---|---|
| Propylene glycol | 60.0 g |
| Polyethylene glycol (average molecular weight 6,000) | 132.0 g |
| Stearyl alcohol | 72.0 g |

Propylene glycol is heated to about 75° C. and nicardipine is dissolved therein. Polyethylene glycol and stearyl alcohol are stirred, one after the other, into the solution at the same temperature and melted. The clear melt is filled into hard gelatine capsules of size 0 of a filling weight of 727 mg, corresponding to 47 mg of nicardipine per capsule.

In-Vitro Liberation Rates

The liberation behavior of the active substance from the drug forms was tested at a constant pH of 1.5 (Values given in % of the amount of active substance present in each case).

TABLE No. 2

|  | Example 11 | Example 12 |
|---|---|---|
| 1 hour | 47% | 25% |
| 2 hours | 68% | 36% |
| 3 hours | 80% | 44% |
| 4 hours | 87% | 50% |
| 5 hours | 92% | 55% |
| 6 hours | 95% | 60% |
| 7 hours | 97% | 64% |

The results from these illustrative studies make it possible, in contradistinction to the prior art, to administer dihydropyridines, particularly those of the kind indicated, in previously uncustomarily high doses once per day (single dose).

These single doses permit increased reliability of the treatment (patient compliance), reduce the frequency of adverse effects, and finally, in view of the simplicity of the method of manufacture, represent an enrichment of the pharmaceutical armamentarium for the treatment of coronary heart disease and high blood pressure.

It will be understood that various changes may be made in the specific techniques and compositions described herein above without departing from the scope of the invention. Accordingly, the preceding description is intended as illustrative only, the scope of the invention being determined solely by the claims appended hereto.

We claim:

1. A solid drug formulation for oral administration comprising one or more dihydropyridines selected from the group consisting of nifedipine, nimodipine, nicardipine, nitrendipine, nisoldipine and felodipine as active substance in a does of 30 to 240 mg and a fatty alcohol or a fatty-alcohol mixture, said dihydropyridine being dissolved in one or more polyethylene glycols having an average molecular weight of 200 to 35,000.

2. The solid drug formulation according to claim 1, wherein the dihydropyridine is present in an amount of 40 to λmg.

3. The solid drug formulation according to claim 1, wherein the nifedipine is present in an amount of 30 to 120 mg.

4. The solid drug formulation according to claim 1 wherein the dihydropyridine is present in non-crystalline form.

5. The solid drug formulation according to claim 1, wherein the ratio of dihydropyridine to polyethylene glycol is 1:2 to 1:50.

6. The solid drug formulation according to claim 1, wherein the ratio of dihydropyridine to polyethylene glycol is 1:4 to 1:40.

7. The solid drug formulation according to claim 6, wherein the fatty alcohol has a chain length of 6 to 30 carbon atoms.

8. The solid drug formulation according to claim 7, wherein the ratio of dihydropyridine to fatty alcohol is 1:0.1 to 1:10.

9. The solid drug formulation according to claim 1, further containing a solubilizer, the ratio of dihydropyridine to solubilizer being 1:0.1 to 1:3.1.

10. The solid drug formulation according to claim 1 in the form of granulates, tablets, pills, coated tablets, capsules, sachets or multi-layer tablets.

11. A method of treating a human patient to effect the remission of symptons associated with coronary heart diseases and/or high blood pressure, which comprises administering to the patient in need of such treatment a solid drug formulation for oral administration comprising one or more dihydropyridines selected from the group consisting of nifedipine, nimodipine, nicardipine, nitrendipine, nisoldipine and felodipine as active substance in a dose of 30 to 240 mg and a fatty alcohol or a fatty-alcohol mixture, said dihydropyridine being dissolved in one or more polyethylene glycols having an average molecular weight of 200 to 35,000.

* * * * *

UNITED STATES PATENT AND TRADEMARK OFFICE
CERTIFICATE OF CORRECTION

PATENT NO. : 5,071,642

DATED : December 10, 1991

INVENTOR(S) : Wolfgang Lahr, et al

It is certified that error appears in the above-identified patent and that said Letters Patent is hereby corrected as shown below:

Claim 1, line 10 column 9, change "does" to --dose--.

Claim 2, line 17 column 9 change "$\lambda$" to --80--.

Claim 11, line 17 column 10 change "symptons" to --symptoms--.

Signed and Sealed this

Thirtieth Day of March, 1993

*Attest:*

STEPHEN G. KUNIN

*Attesting Officer*   Acting Commissioner of Patents and Trademarks